United States Patent [19]

Pearce et al.

[11] Patent Number: 4,607,040

[45] Date of Patent: * Aug. 19, 1986

[54] QUINOLINE DERIVATIVES WHICH ARE 5-HYDROXYTRYPTAMINE ANTAGONISTS

[75] Inventors: Robert J. Pearce, Wilmslow; Craig W. Thornber, Macclesfield, both of United Kingdom

[73] Assignee: Imperial Chemical Industries PLC, London, England

[ * ] Notice: The portion of the term of this patent subsequent to Mar. 6, 2001 has been disclaimed.

[21] Appl. No.: 482,713

[22] Filed: Apr. 6, 1983

[30] Foreign Application Priority Data

Apr. 7, 1982 [GB] United Kingdom ............... 8210261

[51] Int. Cl.⁴ .................... A61K 31/47; C07D 215/22
[52] U.S. Cl. ...................... 514/312; 546/157
[58] Field of Search .............. 424/258; 546/157; 514/312

[56] References Cited

U.S. PATENT DOCUMENTS

| | | | |
|---|---|---|---|
| Re. 16,394 | 7/1926 | Callsen | 546/157 |
| 1,572,768 | 9/1926 | Callsen | 546/157 |
| 1,860,286 | 5/1932 | Hartmann | 546/157 X |
| 4,035,374 | 7/1977 | Durant et al. | 546/153 X |
| 4,235,909 | 11/1980 | Bach et al. | 546/153 X |
| 4,260,764 | 4/1981 | Johnson | 546/153 |
| 4,343,805 | 8/1982 | Crossley et al. | 424/258 X |
| 4,426,387 | 1/1984 | Archibald et al. | 546/153 X |
| 4,435,405 | 3/1984 | Blackburn et al. | 546/157 |

FOREIGN PATENT DOCUMENTS

| | | | |
|---|---|---|---|
| 0430960 | 7/1924 | Fed. Rep. of Germany | 546/157 |
| 0349761 | 6/1931 | United Kingdom | 546/157 |

OTHER PUBLICATIONS

Gilman, et al., J. Am. Chem. Soc., vol. 71, pp. 3667-3668 (1949).
Westland, et al., J. Med. Chem., vol. 16(4), pp. 319-327 (1973).
Zayed, et al., Pharmazie, vol. 33(9), pp. 572-575 (1978).
Soc. Anon. pour l'Ind. a Bale, Chemical Abstracts, vol 26, 3624 (1932).
A. Wander A. G., Chemical Abstracts, vol 43, 7974e (1949).
Aryuzina, et al., Chemical Abstracts, vol 60, 7990f (1964).
Pettit, et al., Chemical Abstracts, vol. 61, 8271f (1964).

Primary Examiner—Donald G. Daus
Assistant Examiner—Diana G. Rivers
Attorney, Agent, or Firm—Cushman, Darby & Cushman

[57] ABSTRACT

Compounds of the formula:

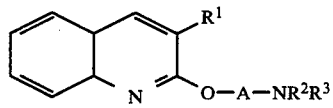

wherein A stands for —$(CH_2)_2$—, which may optionally bear one or two methyl substituents, or for —$(CH_2)_3$—, $R^1$ stands for a defined (3-4C)alkyl radical, a cyclopropyl radical, or a phenyl radical which may optionally bear a defined substituent, and $R^2$ and $R^3$, which may be the same or different, stand for a methyl or ethyl radical, and pharmaceutically-acceptable acid-addition salts thereof. Process for the manufacture of said compounds. Pharmaceutical compositions comprising one of said compounds and a pharmaceutical diluent or carrier. The compounds are 5-hydroxytryptamine antagonists.

8 Claims, No Drawings

QUINOLINE DERIVATIVES WHICH ARE 5-HYDROXYTRYPTAMINE ANTAGONISTS

This invention relates to quinoline derivatives which are active as 5-hydroxytryptamine antagonists in warm-blooded animals.

The compound 2-(2-diethylaminoethoxy)-3-phenylquinoline is described in U.S. Pat. No. 1,860,286, and it is stated therein that it exhibits antipyretic activity. However, there is no reason for one of ordinary skill in the art to deduce from this that compounds of this type would be 5-hydroxytryptamine (5-HT) antagonists.

According to the invention there are provided quinoline derivatives of the formula:

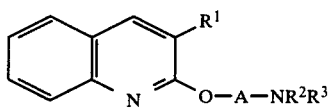   I wherein:
A stands for the radical —$(CH_2)_2$—, which may optionally be substituted by one or two methyl radicals, or for the radical —$(CH_2)_3$—;
$R^1$ stands for an n-, iso- or s-(3–4C)alkyl radical, or a cyclopropyl radical, or it stands for a phenyl radical which may optionally be substituted with a halogen atom or a (1–4C)alkoxy radical; and
$R^2$ and $R^3$, which may be the same or different, stand for a methyl or ethyl radical; and pharmaceutically-acceptable acid-addition salts thereof; but excluding 2-(2-diethylaminoethoxy)-3-phenylquinoline and pharmaceutically-acceptable acid-addition salts thereof.

Some of the compounds of the invention contain at least one asymmetric carbon atom; for example this is the case when A stands for the radical —$(CH_2)_2$— bearing a methyl radical. The racemic form of such compounds containing at least one asymmetric carbon atom can be resolved by conventional methods into the optically active isomers thereof. It is to be understood that the compounds of the invention consist of (a) the compounds of formula I in racemic form, and (b) the optical isomers thereof which are 5-HT antagonists.

A may, for example, stand for a 1,2-ethylene, 1,2-propylene, 2,3-propylene, 1,1-dimethyl-1,2-ethylene, 2,2-dimethyl-1,2-ethylene or 1,3-propylene radical.

$R^1$ may, for example, stand for an n-propyl, isopropyl, n-butyl, s-butyl or cyclopropyl radical. Alternatively, $R^1$ may, for example, stand for a phenyl radical which may optionally be substituted by a fluorine, chlorine or bromine atom or a (1–2C)alkoxy radical, for example a methoxy radical.

One embodiment of the invention consists of quinoline derivatives of the formula I wherein A stands for the radical —$(CH_2)_2$—, which may optionally be substituted by one or two methyl radicals, or for the radical —$(CH_2)_3$—, $R^1$ stands for an n-, iso- or s-(3–4C)alkyl radical, or it stands for a phenyl, halogenophenyl or [(1–2C)alkoxy]phenyl radical, and $R^2$ and $R^3$ stand for a methyl radical, and pharmaceutically-acceptable acid-addition salts thereof.

Suitable salts of the invention are derived from inorganic or organic acids which provide a pharmaceutically-acceptable anion, for example hydrochloric, phosphoric, citric, benzoic, tartaric or succinic acid.

Preferred compounds of the invention are 2-(2-dimethylaminoethoxy)-3-phenylquinoline and pharmaceutically-acceptable acid-addition salts thereof, for example the hydrochloride.

The compounds of the invention, and the compounds used as starting materials in the process of the invention, may be obtained by processes which are known for the preparation of chemically analogous compounds. A compound containing at least one asymmetric carbon atom which is used as a starting material in the process of the invention may be used in a racemic or optically active form.

According to a further feature of the invention there is provided a process for the manufacture of compounds of the formula I, wherein A, $R^1$, $R^2$ and $R^3$ have the meanings stated above, and pharmaceutically-acceptable acid-addition salts thereof, but excluding 2-(2-diethylaminoethoxy)-3-phenylquinoline and pharmaceutically-acceptable acid-addition salts thereof, which comprises reacting a compound of the formula:

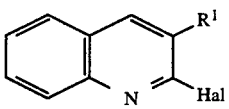   II wherein Hal stands for a halogen atom and $R^1$ has the meaning stated above, with a compound of the formula:

   III wherein A, $R^2$ and $R^3$ have the meanings stated above, or an acid-addition salt thereof, in the presence of an acid-binding agent.

Hal may, for example, stand for a chlorine or bromine atom. The salt of the compound of the formula III may, for example, be a salt derived from an inorganic acid, for example a hydrohalic acid, for example hydrochloric acid. The acid-binding agent may, for example, be sodium hydride. The reaction is conveniently carried out in a suitable organic solvent, for example dimethylformamide, and it may optionally be accelerated or completed by the application of heat.

The activity of compounds of the invention as 5-HT antagonists has been demonstrated in the following tests:

(1) In vitro 5-HT receptor binding (a) Binding of tritiated 5-hydroxytryptamine ([$^3$H]5-HT)

This is an in vitro test of the affinity of test compounds for the central 5-$HT_1$ receptor (Molecular Pharmacology, 1979, 16, 687). The compounds are tested for their ability to displace [$^3$H]5-HT from a receptor site on a synaptosomal preparation prepared from rat brain tissue. The compounds are tested at 3 μg/ml., and they are declared active if they produce more than 30% inhibition of specific binding. Compounds of interest are tested at a range of concentrations to establish the absolute potency for this receptor. The results are expressed in $pI_{50}$ values, the $pI_{50}$ being the $-\log_{10}$ of the concentration of the compound needed to displace 50% of the specifically bound [$^3$H]5-HT.

(b) Binding of tritiated spiroperidol ([³H]spiroperidol)

This is an in vitro test of the affinity of test compounds for the central 5-HT₂ receptor (Molecular Pharmacology, 1979, 16, 687). The compounds are tested for their ability to displace [³H] spiroperidol from a receptor on a synaptosomal preparation prepared from rat brain cortex. The compounds are tested at 0.3 μg./ml., and they are declared active if they produce more than 30% inhibition of specific binding. Compounds of interest are tested at a range of concentrations as outlined above in respect of [³H]5-HT binding. The results are expressed as $pI_{50}$ values, the $pI_{50}$ being the $-\log_{10}$ of the concentration of the compound needed to displace 50% of the specifically bound [³H]spiroperidol.

(2) Inhibition of head twitches induced in mice by 5-hydroxytryptophan (5-HTP)

This is an in vivo test of activity at central 5-HT receptors. The test involves administering a precursor of 5-HT, i.e. 5-HTP, to mice. The resultant high levels of 5-HT produced in the brain are believed to be responsible for the spontaneous twitching of the head and ears seen for a period after the administration of 5-HTP. All known centrally acting 5-HT antagonists inhibit the twitching response in a dose-dependent manner.

A range of doses of the compounds under test are administered intraperitoneally to male mice (average weight 18–20 g.; in groups of 5) 15 minutes before an intra-peritoneal injection of 5-HTP at 300 mg./kg. The mice are then observed 15 minutes later for head twitches, and the results are expressed as $ID_{50}$ values. Non specific inhibition of the response due, for example, to sedation is eliminated by determining the presence or absence of the pinna reflex to tactile stimulation of the ear.

(3) Antagonism of fenfluramine-induced hyperthermia in rats

This is a sensitive in vivo test which is based on the ability of fenfluramine to release 5-HT from endogenous neuronal stores.

Female rats (Alderley Park Strain; 180–220 g.) are housed (5 per cage) in a relatively warm environment (25°–28° C.) one hour prior to the beginning of the test to allow the animals to acclimatise. When the acclimatisation period is over, the rectal temperature of each animal is measured and these temperatures serve as the control reading from which all changes are calculated. For the recording of the control temperatures ($-1$ hour), either a test compound or the vehicle (distilled water) is administered orally or subcutaneously, and after a further hour (0 hour) the rectal temperature of each rat is measured. A dose of 15 mg./kg. of fenfluramine, or distilled water (controls), is then injected intraperitoneally. Rectal temperatures are then measured at the following times after the administration of the fenfluramine or distilled water:

30 minutes, and 1, 2, 3, 4, 5 and 6 hours

The potency of a compound in the test is expressed as an $ID_{50}$ value, i.e. the dose of the compound which reduces the hyperthermic response to a standard dose of fenfluramine by 50%.

The potency of a specific compound of the present invention depends upon its precise chemical structure, but generally speaking the compounds of the invention exhibit the following potencies in the following ranges in the above tests:

Test (1)(a): [³H]5-HT binding: $pI_{50}$ 5–9
Test (1)(b): [³H]spiroperidol binding: $pI_{50}$ 5–9
Test (2): $ID_{50}$ 0.1 to 50 mg./kg.
Test (3): $ID_{50}$ 0.1 to 50 mg./kg.

No toxic effects or other undesirable effects have been observed with the compounds at doses at which they are active in the above-mentioned tests. Furthermore, as an indication of the lack of toxicity of a specific compound of the invention, namely 2-(2-dimethylaminoethoxy)-3-phenylquinoline hydrochloride, that compound has been tested in a multi-observational battery of central nervous system tests in the mouse, and no evidence of toxicity was seen at oral doses up to 100 mg./kg.

Because of their activity as 5-HT antagonists the compounds of the invention may be used clinically in human patients as psychotropic agents for the treatment of diseases or dysfunctions of the central nervous system, for example psychoses, schizophrenia, mania, anxiety or depression, for the treatment of migraine, urticaria, asthma, hypertension, pulmonary hypertension, vascular spasm and gastrointestinal disorders, and for the inhibition of the aggregation of blood platelets. When one of the said compounds is used clinically in human patients it is recommended that it be dosed:

(a) orally at a dose of 0.5 mg./kg. to 100 mg./kg. at suitable intervals, for example three times per day, or (b) intramuscularly at a dose of 0.1 mg./kg. to 20 mg./kg. at suitable intervals, (c) by means of a depot injection (2.5 to 100 mg./kg.), or (d) rectally at a dose of 0.5 mg./kg. to 200 mg./kg.

According to a further feature of the invention there are provided pharmaceutical compositions comprising a compound of the formula I wherein A, R¹, R² and R³ have the meanings stated above, or a pharmaceutically-acceptable acid-addition salt thereof, but excluding 2-(2-diethylaminoethoxy)-3-phenylquinoline or a pharmaceutically-acceptable acid-addition salt thereof, and an inert pharmaceutically-acceptable diluent or carrier.

The pharmaceutical compositions of the invention may be in a form suitable for oral, parenteral or rectal administration. Thus, for example, they may be in orally-administrable unit dosage form, for example tablets or capsules, which may optionally be adapted for sustained release, or in injectable form, for example a sterile injectable solution or suspension, or in the form of a suppository for rectal administration. The said pharmaceutical compositions may be produced by conventional methods using conventional diluents and carriers.

The pharmaceutical compositions of the invention may contain, in addition to a compound of the formula I, wherein A, R¹, R² and R³ have the meanings stated above, or a pharmaceutically-acceptable acid-addition salt thereof, one or more of the following medicaments:

1. known psychotropic agents, for example antipsychotic agents, for example chlorpromazine, haloperidol or fluphenazine, or antidepressants, for example imipramine, mianserin or desmethylamitryptyline;

2. known anti-migraine agents, for example ergot alkaloids and derivatives thereof, and propranolol, clonidine, pitzotifen, O-acetylsalicyclic acid or paracetamol;

3. known antihypertensive agents, for example α-methyldopa, α-adrenergic blocking agents, for example prazosin, β-adrenergic blocking agents, for example propranolol or atenolol, diuretics, for example hydrochlorothiazide or frusemide, and vasodilators, for example minoxidil or hydrallazine; and 4. known platelet aggregation inhibitors, for example dipyridamol, anturan, sulphinpyrazone, ticlopidine and O-acetylsalicylic acid.

The invention is illustrated but not limited by the following Examples in which the temperatures are expressed in degrees Celsius and the petroleum ether had b.p. 60°–80°:

EXAMPLE 1

2-Dimethylaminoethanol (1.07 g.) was added dropwise to a suspension of sodium hydride (0.56 g. of a 50% w/w dispersion in mineral oil) in dimethylformamide (25 ml.) at 0°–5°. When all the hydrogen had evolved, 2-chloro-3-phenylquinoline (2.5 g.) was added and the mixture was stirred and heated at 75° for 12 hours. The mixture was then cooled to ambient temperature, poured into ice-water (500 ml.), and extracted with ethyl acetate (5 × 100 ml.). The ethyl acetate extract was washed successively with water (50 ml.) and saturated brine (50 ml.), and then dried (MgSO$_4$). The solvent was evaporated under reduced pressure (approx. 15 mm.) and the residual oil was chromatographed on basic alumina (100 g.; Brockmann Grade III), eluted with increasing concentrations of chloroform in petroleum ether. The eluate obtained with 10% v/v chloroform in petroleum ether was evaporated. The residual oil was dissolved in diethyl ether (100 ml.), and ethereal hydrogen chloride was added until precipitation was complete The mixture was filtered and the solid residue was crystallised from ethanol-diethyl ether to give 2-(2-dimethylaminoethoxy)-3-phenylquinoline hydrochloride, m.p. 155°–7°.

EXAMPLE 2

2-Dimethylaminoethanol (1.07 g.) was added dropwise to a suspension of sodium hydride (0.56 g. of a 50% w/w dispersion in mineral oil) in dimethylformamide (25 ml.) at 0°–5°. When all the hydrogen had evolved, 2-chloro-3-(4-fluorophenyl)quinoline (2.69 g.) was added and the mixture was stirred at ambient temperature for 16 hr. The mixture was then poured into ice-water (500 ml.) and extracted with ethyl acetate (5 × 100 ml.). The ethyl acetate extract was washed successively with water (50 ml.) and saturated brine (50 ml.), and then dried (MgSO$_4$). The solvent was evaporated under reduced pressure and the residual oil was chromatographed on basic alumina (100 g.; Brockmann Grade III), eluted with increasing concentrations of ethyl acetate in petroleum ether. The eluate obtained with 10% v/v ethyl acetate in petroleum ether was evaporated. The residual oil was dissolved in diethyl ether (100 ml.), and ethereal hydrogen chloride was added until precipitation was complete. The mixture was filtered and the solid residue was crystallised from methanol-ethyl acetate to give 2-(2-dimethylaminoethoxy)-3-(4-fluorophenyl)quinoline hydrochloride, m.p. 168°–171°.

EXAMPLES 3 to 5

The procedure described in Example 2 was repeated except that the indicated amounts of the following starting materials were used, and there were thus obtained: from 2-dimethylaminoethanol (1.07 g.) and 2-chloro-3-(2-methoxyphenyl)quinoline (2.81 g.), 2-(2-dimethylaminoethoxy)-3-(2-methoxyphenyl)quinoline hydrochloride, m.p. 130°–2° (Example 3); from 2-dimethylaminoethanol (1.07 g.) and 2-chloro-3-isopropylquinoline (2.27 g.), 2-(2-dimethylaminoethoxy)-3-isopropylquinoline hydrochloride, m.p. 167°–171° (Example 4); and from 2-dimethylamino-2-methylpropanol (1.41 g.) and 2-chloro-3-phenylquinoline (2.5 g.), 2-(2-dimethylamino-2-methylpropoxy)-3-phenylquinoline hydrochloride, m.p. 183°–4° (Example 5).

EXAMPLE 6

The procedure described in Example 2 was repeated except that, instead of 2-dimethylaminoethanol and 2-chloro-3-(4-fluorophenyl)quinoline, the starting materials were 3-dimethylaminopropanol (1.24 g.) and 2-chloro-3-phenylquinoline (2.5 g.), and the eluant used in the chromatography was petroleum ether rather than increasing concentrations of ethyl acetate in petroleum ether. There was thus obtained 2-(3-dimethylaminopropoxy)-3-phenylquinoline hydrochloride, m.p. 184°–6°.

EXAMPLE 7

Sodium hydride (0.48 g. of a 50% w/w dispersion in mineral oil) was added to a solution of 2-dimethylaminopropanol (1.1 g.) in dimethylformamide (20 ml.) at ambient temperature. When all the hydrogen had evolved, 2-chloro-3-phenylquinoline (2.4 g.) was added and the mixture was stirred at ambient temperature for 16 hr. The mixture was poured into water (200 ml.), and extracted with ethyl acetate (2 × 100 ml.). The ethyl acetate extract was washed with water (50 ml.) and then dried (MgSO$_4$). The solvent was evaporated under reduced pressure and the residual oil was chromatographed on basic alumina (100 g.; Brockmann Grade III), eluted with increasing concentrations of chloroform in petroleum ether. The eluate obtained with 20% v/v chloroform in petroleum ether was evaporated. The residual oil was dissolved in diethyl ether (50 ml.), and ethereal hydrogen chloride was added until precipitation was complete. The mixture was filtered and the solid residue was precipitated from ethyl acetate-diethyl ether to give 2-(2-dimethylaminopropoxy)-3-phenylquinoline hydrochloride, m/z 305 [(M-H)$^+$; calculated for $C_{20}H_{21}N_2O$ is 305.1654, found 305.1654].

What we claim is:

1. A quinoline derivative of the formula:

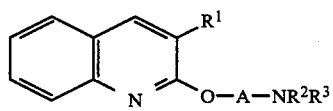

wherein:
A is a member selected from the group consisting of —(CH$_2$)$_2$—, —(CH$_2$)$_2$— which is substituted by not more than two methyls, and —(CH$_2$)$_3$—;
R$^1$ is a member selected from the group consisting of n-, iso- and s-(3–4C)alkyl, cyclopropyl, phenyl, halogenophenyl and [(1–4C)alkoxy]phenyl; and
R$^2$ and R$^3$ are each methyl;
or a pharmaceutically-acceptable acid-addition salt thereof.

2. A compound as claimed in claim 1 wherein A is a member selected from the group consisting of 1,2-ethylene, 1,2-propylene, 2,3-propylene, 1,1-dimethyl-1,2-ethylene, 2,2-dimethyl-1,2-ethylene and 1,3-propylene.

3. A compound as claimed in claim 1 wherein R$^1$ is a member selected from the group consisting of n-propyl, isopropyl, n-butyl, s-butyl, cyclopropyl, phenyl, fluorophenyl, chlorophenyl, bromophenyl and [(1-2C)alkoxy]-phenyl.

4. A compound as claimed in claim 1 wherein A is a member selected from the group consisting of —(CH$_2$)$_2$—, —(CH$_2$)$_2$- which is substituted by not more than two methyls, and —(CH$_2$)$_3$—, and R$^1$ is a member selected from the group consisting of n-, iso- and s-(3-4-C)alkyl, phenyl, halogenophenyl and [(1-2C)alkoxy]-phenyl.

5. A compound as claimed in claim 1 which is a member selected from the group consisting of 2-(2-dimethylaminoethoxy-3-phenylquinoline and pharmaceutically-acceptable acid-addition salts thereof.

6. A compound as claimed in claim 5 which is 2-(2-dimethylaminoethoxy)-3-phenylquinoline hydrochloride.

7. A pharmaceutical composition for use as a 5-hydroxytryptamine antagonist, comprising an effective amount of a quinoline derivative of the formula I, wherein A, R$^1$, R$^2$ and R$^3$ have the meanings stated in claim 1, or a pharmaceutically-acceptable acid-addition salt thereof, and an inert pharmaceutically-acceptable diluent or carrier.

8. In a method of treatment which requires the use of a 5-hydroxytryptamine antagonist, the improvement which comprises using, as the antagonist, an effective amount of a compound according to claim 1.

* * * * *